United States Patent
Davis

(10) Patent No.: US 6,651,502 B1
(45) Date of Patent: Nov. 25, 2003

(54) METHOD FOR ACOUSTIC IMAGING OF A TUBULAR SHAPE

(75) Inventor: William R. Davis, Hollywood, MD (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 10/114,387

(22) Filed: Apr. 3, 2002

(51) Int. Cl.$^7$ ................................................ G01N 9/24
(52) U.S. Cl. ........................................................ 73/606
(58) Field of Search .......................... 73/606, 622, 602; 367/7

(56) References Cited

U.S. PATENT DOCUMENTS

| | | | |
|---|---|---|---|
| 3,654,596 A | * | 4/1972 | Osepchuk ....................... 367/7 |
| 4,165,649 A | | 8/1979 | Greer |
| 4,221,132 A | | 9/1980 | Poole |
| 4,270,389 A | | 6/1981 | Shiraiwa et al. |
| 4,297,886 A | * | 11/1981 | Anikeev et al. ............... 73/642 |
| 4,434,660 A | | 3/1984 | Michaels et al. |
| 4,435,984 A | | 3/1984 | Gruber |
| 4,531,411 A | | 7/1985 | Collins et al. |
| 4,625,557 A | * | 12/1986 | Rutherford ................... 73/635 |
| 4,679,437 A | | 7/1987 | Koike et al. |
| 5,165,280 A | | 11/1992 | Sternberg et al. |
| 5,483,963 A | | 1/1996 | Butler et al. |
| 5,526,689 A | | 6/1996 | Coulter et al. |
| 5,568,448 A | | 10/1996 | Tanigushi et al. |
| 5,686,668 A | | 11/1997 | Mccean |
| 5,698,854 A | | 12/1997 | Gupta |
| 5,969,255 A | | 10/1999 | Mccean |
| 6,005,827 A | | 12/1999 | Hossack et al. |
| 6,016,285 A | | 1/2000 | Wright et al. |
| 6,030,344 A | | 2/2000 | Guracar et al. |
| 6,036,643 A | | 3/2000 | Criton et al. |
| 2002/0117004 A1 | * | 8/2002 | Satoh .......................... 73/618 |

FOREIGN PATENT DOCUMENTS

JP          05215727 A    *  8/1993  .......... G01N/29/10

* cited by examiner

Primary Examiner—Hezron Williams
Assistant Examiner—Tamiko Bellamy
(74) Attorney, Agent, or Firm—Mark O. Glut

(57) ABSTRACT

A method for acoustic imaging of a tubular shape, the tubular shape having an outer surface and an inner surface. The method includes directing an ultrasonic beam through a focusing lens. The focusing lens has a planar edge and a concave edge located on opposite sides of the focusing lens. The ultrasonic beam enters the focusing lens through the planar edge and exits from the concave edge such that the ultrasonic beam enters the outer surface of the tubular shape, passes to the inner surface and the beam is reflected at the inner surface, passes through the outer surface and through the focusing lens in the opposite direction. The ultrasonic beam that has passed through the focusing lens in the opposite direction is then converted into a video output that displays an image of the inner surface, the outer surface and an internal volume image of the tubular shape.

19 Claims, 4 Drawing Sheets

METHOD FOR ACOUSTIC IMAGING OF A TUBULAR SHAPE

CROSS-REFERENCE TO RELATED PATENTS

The above listed invention is hereby cross-referenced and related to U.S. Pat. No. 6,543,287 issued Apr. 8, 2003, entitled "Method for Acoustic Imaging by Angle Beam" (Navy Case 80281) by inventor William R. Davis. U.S. Pat. No. 6,543,287 is not admitted to be prior art with respect to the present invention. U.S. Pat. No. 6,543,287 is hereby incorporated by reference. Both inventions are assigned to the same assignee and have been invented by the same inventor.

STATEMENT OF GOVERNMENT INTEREST

The invention described herein may be manufactured and used by or for the Government of the United States of America for governmental purposes without payment of any royalties thereon or therefor.

BACKGROUND

Nondestructive inspection ("NDI") is a field which includes all means of evaluating the quality and strength of materials and structures without adversely affecting their quality, strength or usefulness. NDI usually includes methods recognized by the American Society of Nondestructive Testing ("ASNT"). These methods include, but without limitation, radiography, eddy current testing, dye penetrant testing, ultrasonic testing, leak testing, thermography, and the like. These methods help find cracks, corrosion, weld flaws, rolling or processing flaws, thickness variations and various other imperfections or discontinuities that may affect quality and strength of a material or structure.

Detection and discrimination of the type of imperfections or discontinuities on the interior or inside surface of a tubular shape is difficult even with all the presently available testing when only the exterior is accessible. Even ultrasonic inspection with a single crystal search unit does not clearly indicate the type of discontinuity or imperfection.

A method that can be utilized to inspect the inner surface of a tubular shape is real time imaging of ultrasound waves. Real time imaging of ultrasound waves can utilize a modified Charge Coupled Device ("CCD") camera. Any other device capable of imaging ultrasound waves or beams may also be utilized. The camera provides images with normal television framing rates of 100% of the interior parts. The method utilizes high frequency sound waves or beams (ultrasound) instead of ionizing radiation. Sound beams are passed through the test piece (the tubular shape) being inspected and are partially attenuated by discontinuities and imperfections. The internal volume of the test piece is therefore imaged as in radiography (volumetric inspection). This then provides a shadowgraph display similar to a real time X-ray except that no ionizing radiation is present. Unlike radiographic (X-ray) methods, sound waves are strongly blocked by cracks, voids and other interfacial discontinuities. This provides higher sensitivity to critical and potentially dangerous discontinuities or imperfections.

The real time imaging of ultrasonic waves or beams typically utilizes one of three methods. The first method passes the sound beam entirely through the test piece, material or structure (through transmission). The second method introduces the sound beam from the front of the test piece (perpendicular to it) and then images the part of the beam reflected back to the camera. The third method introduces the sound beam into the test piece at an angle so that the reflection from a surface of the test piece (a specular reflection) is imaged by the camera (or a camera chip). The difficulties preventing the present art from accomplishing the imaging of the inner surface of a tubular shape is the scatter of the ultrasonic beam by the curved pipe surfaces and the relatively strong reflection from the outer surface, which obscures the weaker reflection from the inner surface of the tubular shape. Thus there exists the need for a method or apparatus that may be used to inspect a tubular shape, particularly, to inspect the inner surface of a tubular shape and may be used when only the outside or exterior surface of the tubular shape is accessible.

For the foregoing reasons, there is a need for a new method for acoustic imaging of a tubular shape that can quickly inspect the inner or interior surface and outer or exterior surface of a tubular shape and discern small discontinuities before they can cause failure.

SUMMARY

The instant invention is directed to a method for acoustic imaging of a tubular shape that satisfies the needs enumerated above and below.

The present invention is directed to a technique for the inspection of a tubular shape or a tubular test piece of various wall thickness. A tubular shape is, but without limitation, typically defined as a hollow cylinder, and typically used for conveyance of a fluid (gas or liquid). A tubular shape may also be a cylinder or drum with closed ends used for liquid or gas storage. A tubular shape may also be referred to, but without limitation, as a tubular product, tubing, a conduit, a pipe, piping, a channel, a tube, a hollowed beam, a fluid conveyor, or a hose. Typically tubular shapes are manufactured from metals, metal alloys, rubber, ceramics, plastics, polyvinyl chloride (PVC), or any type of material that lends itself to storing, conveying, or transporting fluids.

The present invention utilizes real time ultrasonic imaging in a new and unique way. The ultrasonic sound beam is initiated by an ultrasonic transducer and directed through a focusing lens of unique design to redirect the beam through the outer surface of the tubular shape and into the tubular shape wall. The ultrasonic beam is then reflected at the inner surface of the tubular shape, passes back through the outer surface of the tubular shape, through the same or another focusing lens in the opposite direction and to an imaging camera chip separate from and lying more or less beside the initiating transducer. The imaging camera chip then converts the ultrasonic beam into an image of the inner surface, the outer surface and an internal volume image of the tubular shape.

There are two primary methods to direct the beam to and through the tubular shape. The first method utilizes an angle beam arrangement. In the angle beam arrangement, the beam is directed through the outer surface of the tubular shape and into the tubular shape, not perpendicular to the outer surface, but at an oblique angle to the outer surface or at an oblique angle to a line drawn vertical to the outer surface of the tubular shape.

A second method utilizes the same focusing lens design but utilizes a beam splitter arrangement. In this method the sound beam is directed through the lens along a line perpendicular to the surface of the tubular shape or perpendicular to a line drawn vertical to the outer surface of the tubular shape. The sound beam passes through the outer surface of the tubular shape and changes direction by refraction (refraction is defined, but without limitation, as a change of direction of rays, beams, or waves which are obliquely incident upon and pass through a surface bounding two media in which the ray, beam or wave has different velocities.) The sound beam passes from the outer surface to the inner surface and reflects from the inner surface. It passes through the tubular shape wall and again through the outer surface, being refracted there. It then passes back through the focusing lens and to the imaging camera chip. The beam in this instance strikes the inner surface at a 90-degree angle. In both methods, the reflection from the outer surface and the inner surface are both imaged but can in many instances be separated electronically by range gating.

It is an object of the invention to provide a method for acoustic imaging of a tubular shape that is a nondestructive inspection technique.

It is an object of the invention to provide a method for fast inspection of the inner (interior) surface of a tubular shape when the tubular shape is either empty or full of fluid.

It is an object of the invention to provide a method for acoustic imaging a tubular shape that may be used to inspect the inner and outer surface of a tubular shape when only the outside surface is accessible.

DRAWINGS

These and other features, aspects and advantages of the present invention will become better understood with reference to the following description and appended claims, and accompanying drawings wherein:

DESCRIPTION

Figure 1:
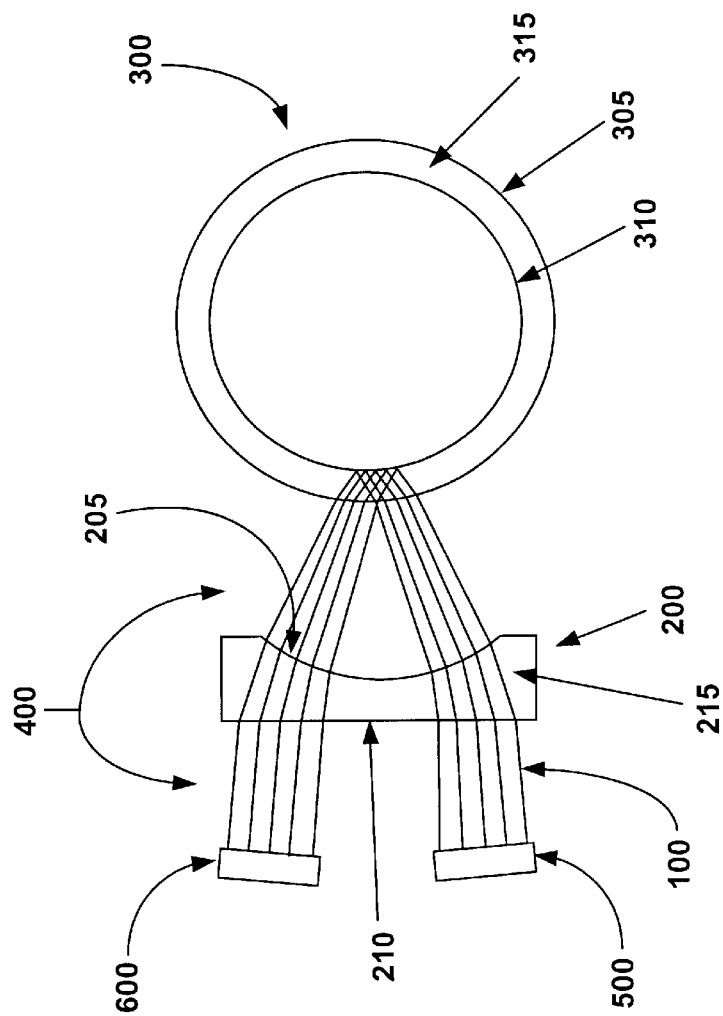
FIG. 1 is a representation of one of the embodiments of the method for acoustic imaging of a tubular shape (utilizing the angle beam arrangement)

The preferred embodiments of the present invention are illustrated by way of example below and in FIGS. 1, 2, 3 and 4. As seen in FIG. 1, the method includes directing an ultrasound or ultrasonic beam 100 or wave through a focusing lens 200 toward a test piece to be inspected; in this example, the test piece is a pipe 300 manufactured from metal. It is to be understood, however, that many types of anomalies in many types of test pieces or media can be reliably detected as is described and claimed herein. Furthermore, the method is not limited to ultrasonic beams or waves, but rather other mechanical, electrical, or acoustical waves can be utilized where practicable. This method may be utilized for any type of shape that is substantially tubular and manufactured from a variety of products. The tubular shape could be, but without limitation, a pipe, plumbing, a conduit, a shunt, a shaft, a rod, a cantilever or even possibly a bone, human or otherwise.

The pipe 300 or tubular shape being inspected typically has an exterior or outer surface 305, an interior or inner surface 310 and a pipe interior 315. The pipe interior 315 is located between the outer surface 305 and the inner surface 310 of the pipe 300. As seen in FIG. 1, the outer surface 305 and inner surface 310 may be substantially circular or substantially annular and substantially axially aligned.

The ultrasonic beam 100 enters and passes through the focusing lens 200 such that upon exiting the focusing lens 200 the ultrasonic beam 100 enters the outer surface 305 of the pipe 300 at some angle to a line drawn vertical to the outer surface 305. An angle to a line drawn vertical to the outer surface 305 is equal to zero (perpendicular to the outer surface 305) for the beam splitter arrangement and something other than zero (oblique) for the angle beam arrangement.

FIG. 1 shows a representation of the invention utilizing the angle beam arrangement where the angle to a line drawn vertical to the outer surface 305 is something other than zero. In this embodiment, the ultrasonic beam 100 enters the outer surface 305 of the pipe 300 at some oblique angle to a line drawn vertical to the outer surface 305 or at an oblique angle to the outer surface 305, then passes through the pipe interior 315 and is reflected at the inner surface 310, back through the pipe interior 315, through the outer surface 305 and then passes through the focusing lens 200 in the opposite direction to an imaging chip 600. The ultrasonic beam 100 is then converted into a video output by the imaging chip 600. The video output displays an image of the inner surface 310, the outer surface 305 and an internal volume image of the pipe 300.

Figure 2:
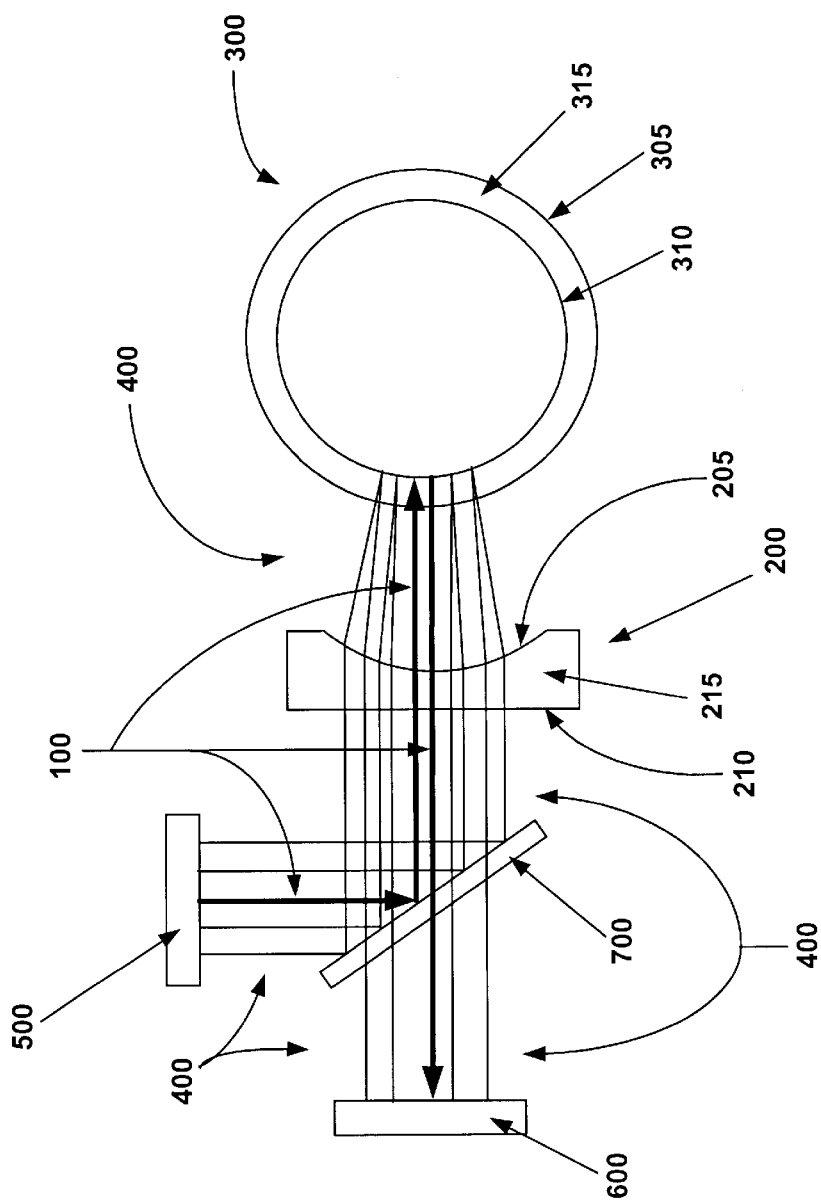
FIG. 2 is a representation of one of the embodiments of the method for acoustic imaging of a tubular shape (utilizing the beam splitter arrangement)

In another embodiment, as seen in FIG. 2, the ultrasonic beam 100 enters the outer surface 305 along a line perpendicular to the outer surface 305 of the pipe 300 or at a 90 degree angle (perpendicular) to a line drawn vertical to the outer surface 305. In a preferred embodiment, the ultrasonic beam 100 is reflected from its path by a beam splitter 700 prior to the ultrasonic beam 100 entering the focusing lens 200. A beam splitter 700 is defined, but without limitation, as an apparatus that changes the path of an ultrasonic beam In the preferred embodiment the beam splitter 700 is placed at about a 45-degree angle to the path of the ultrasonic beam 100. This embodiment can be referred to as the beam splitter arrangement of the invention. The ultrasonic beam 100 enters the outer surface 305 and strikes the inner surface 310 at about a 90-degree angle.

In the preferred embodiment, whether utilizing the angle beam arrangement or the beam splitter arrangement, the ultrasonic beam 100 passes through a medium 400 through the entire method when not passing through the focusing lens 200 or the internal volume of the pipe 300. The medium 400 may be liquid or solid.

The ultrasonic beam 100 may generated in a variety of ways. For instance, but without limitation, an ultrasonic transducer fabricated from a piezoelectric crystal may be used to generate the ultrasonic beam 100. A transducer 500 is any device or element that converts an input signal into an output signal of a different form. An ultrasonic transducer will provide the best results. Ultrasonic transducers can be piezoelectric, electromagnetic, electrostatic, magnetostatic, laser, optical, or any other type. A piezoelectric transducer is optimal and typically consists of a piezoelectric element in the form of a wafer cut from a single (natural) crystal. The piezoelectric transducer typically creates a piezoelectric effect, which is a phenomenon in which an impressed electronic signal produces a mechanical vibration or ultrasonic beam 100 in a material or medium. The piezoelectric effect causes the crystal to vibrate preferentially at the natural resonant frequency of the crystal as fabricated in a metallic housing.

The preferred method of initiating an ultrasonic beam 100 and imaging the ultrasonic beam 100 utilizes a Charge Couple Device ("CCD") acoustic imaging camera. An example of a CCD camera that may be utilized in this invention is described in U.S. Pat. No. 5,483,963, "Two Dimensional Transducer Integrated Circuit" by Neal Butler and Marvin Lasser. Any other device capable of generating and imaging ultrasound waves or beams may also be utilized.

A timing signal from a Charge Couple Device acoustic imaging camera may be sent to a digital delay circuit, which delays the timing signal for a programmed amount of time and then transmits the timing signal to an electronic pulser circuit. Then an electronic pulse of programmed amplitude and shape is generated by the electronic pulser circuit, and the electronic pulse is transmitted to a transducer 500. The transducer 500 then converts the electronic pulse into an ultrasonic beam 100. The electronic pulse can be transmitted via a wire, conduit, channel or any electric/electronic transmitting material. The preferred programmed amount of delay time is an amount of time required for the electronic pulser circuit to generate an electrical pulse, send the pulse to the transducer 500, for the transducer 500 to change the electrical signal into an ultrasonic beam 100, for the ultrasonic beam 100 to travel to and through the focusing lens 200, to and through the tubular shape 300, back to and through the focusing lens 200, and to the Charge Couple Device acoustic imaging camera.

The CCD acoustic imaging camera is a Charge Coupled Device camera that is modified to detect pressure waves rather than light waves. The Charge Coupled Device uses integrated circuitry to transfer a signal along a row of discrete picture elements (or pixels). The CCD acoustic imaging camera can be an adaptation of an infrared focal plane array and electronics. The focal plane array can be a hybrid fabricated from polyvinyl difluoride (PVDF) spun coated on to a CCD imaging array. Other devices such as microfabricated or multielement ultrasonic transducers might also be utilized for imaging.

The electronic pulse of programmed amplitude and shape is tailored to the type of modified CCD imaging array (or other imager) being utilized. A CCD imaging array that is bipolar and is affected by negative pressure (losing charge or energy) requires a longer positive pressure wave to maximize signal intensity. A CCD imaging array, which can differentiate between positive and negative pressure, can change the sign of the negative pressure to make the two additive. It may utilize sound pressure in the form of a true sine wave. Any electronic circuit that outputs voltage and wave shape can be used.

After the sound wave is initiated via piezoelectric effect by the transducer 500, the wave front exiting the transducer 500 is changed into an ultrasonic beam 100, which is a physical (strain) wave in a solid or a compression wave in a liquid (depending on the medium 400 the wave is traveling through). The ultrasonic beam 100 (the physical (strain) wave or compression wave) passes through a focusing lens 200 uniquely designed for the pipe 300 or tubular shape being inspected. The ultrasonic beam 100 is coupled or projected to the outer surface 305 of the pipe 300 via a physically continuous path, conductor, or medium 400 composed of a solid or a liquid. The ultrasonic beam 100 is coupled to the outer surface 305 such that the ultrasonic beam 100 enters the outer surface 305 and progresses along a vector to the inner surface 310 of the pipe 300. The ultrasonic beam 100 enters the pipe 300 and outer surface 305 at an oblique angle or a right angle to a line drawn vertical to the outer surface 305 of the pipe 300 or at an oblique or right angle to the outer surface 305 (depending on the arrangement utilized). When utilizing the angle beam arrangement, the angle is typically a non-parallel and non-perpendicular or an oblique angle to the outer surface 305. When utilizing the beam splitter arrangement, the angle is typically substantially perpendicular or about 90 degrees to the outer surface 305. The ultrasonic beam 100 passes through the pipe interior 315 and is reflected at the inner surface 310, progresses along a vector to the outer surface 305 of the pipe 300, is refracted as it passes into the medium 400 and passes through a different portion of the same focusing lens 200 it passed through initially, or a second similar focusing lens placed adjacent to the first focusing lens. The ultrasonic beam 100 exits the focusing lens 200 and progresses to an imaging camera chip 600 communicating with a CCD acoustic camera or other imaging device, where the ultrasonic beam energy is changed into an image by the imaging camera chip 600. When the ultrasonic beam 100 is initially projected toward the test piece or pipe 300, the reflection from the outer surface 305 to the camera does not reach the imaging chip because of the design of the focusing lens 200. In many instances, the first reflection can be of much greater amplitude and may prevent detection of second surface reflections or may cause confusion in the interpretation of the image. The design and shape of the focusing lens prevents this problem and allows the entire pipe 300 or test piece to be imaged.

Using the beam splitter arrangement, as seen in FIG. 2, the ultrasonic beam 100 from the transducer 500 is reflected by a beam splitter 700 that is disposed at about a 45 degree angle to the path of the ultrasonic beam 100. The ultrasonic beam 100 then passes through a focusing lens 200 uniquely designed for the pipe 300 or tubing being inspected. Then the ultrasonic beam 100 is coupled or projected to the outer surface 305 of the pipe 300 via a physically continuous path or conductor or coupling medium 400 composed of a solid or a liquid. The ultrasonic beam 100 is coupled at an angle such that the ultrasonic beam 100 is at about 90 degrees or substantially perpendicular to the outer surface 305 and progresses along a vector to the inner surface 310 of the pipe 300. The ultrasonic beam 100 strikes the inner surface 310 at about 90 degrees or is substantially perpendicular to the inner surface 310. The ultrasonic beam 100 is reflected at the inner surface 310, progresses along a vector to the outer surface 305 of the pipe 300, passes into the coupling media 400 and passes through the same portion of the same focusing lens 200 it passed through initially. The ultrasonic beam 100 exits the focusing lens 200 and progresses to an imaging camera chip 600 communicating with a CCD acoustic camera or readout electronic circuitry, where the ultrasonic beam energy is changed into an image. The images of both the outer and inner surface and the volume of the object are included in the CCD image.

The medium 400 or continuous path or conductor may be liquid or solid. A medium 400 or continuous path or conductor for ultrasonic beams 100 or waves is used because the medium/continuous path/conductor enables travel of the ultrasonic beam 100 to the point of interest without undue attenuation. Any type of liquid may be used as a medium 400, such as, but without limitation, water, glycerin, grease, alcohol, oil, any kind of paste (such as wall paper paste or toothpaste), or any type of gel. Water is usually the easiest and most convenient. The liquid must contain few bubbles, which can block or distort the wave. Any solid may be used, but using a solid that is the same material as the test piece or pipe 300 produces the best results, because there is minimal refraction or reflection of the ultrasonic beam 100 at the interface of the pipe 300 and medium 400. The pipe 300, the focusing lens 200, the transducer 500, the beam splitter 700 (when utilizing the beam splitter arrangement), and the imaging chip 600 may be submerged in a water filled tank and the ultrasonic beam 100 would thus travel through the water, with the water acting as the medium 400.

The portion of the ultrasonic beam 100 or wave that is exiting the pipe 300 is focused by the focusing lens 200 such that the ultrasonic beam 100 travels to an imaging area within the CCD acoustic imaging camera, where it is transformed by readout electronics into electronic signals. Additional focusing lenses between the focusing lens 200 and the CCD acoustic imaging camera may be utilized to form the image on the CCD acoustic-imaging camera.

The focusing lens 200 may be an acoustic lens. An acoustic lens is a lens for focusing acoustic waves or ultrasonic beams. The focusing lens 200 can be circular or non-circular in contour. An acoustic lens can focus a beam or wave of sound onto a specific point or line, allowing a very weak sound to be more easily heard. It also can be used to focus sound from one point onto another. The focusing lens 200 is used to directly focus the sound onto the test piece or pipe 300 and the imaging area and will allow a weak signal to be more easily heard. The focusing lens 200 may be fabricated from any homogeneous material that does not cause random distortions of waves. The focusing lens 200 can be manufactured, but without limitation, from plastic, glass, ceramic, Lucite (™), Plexiglas (™) or any material that has a different acoustic velocity from that of the medium 400 and allows refraction to occur.

As seen in FIGS. 1 and 2, the preferred focusing lens 200 is a plano-concave lens. The focusing lens 200 may have a concave edge 205, a planar edge 210, and an interior portion 215. The focusing lens 200 may have a substantially rectangular shape. The concave edge 205 and the planar edge 210 may be disposed on opposite sides of the focusing lens 200. The planar edge 210 is substantially straight and substantially flat; however, it may be mildly concave or mildly convex. As shown in FIGS. 1 and 2, the ultrasonic beam 100 exits the transducer 500 passes through the medium 400, enters the focusing lens 200 through the planar edge 210, passes through the interior portion 215 of the focusing lens 200, and exits the focusing lens 200 from the concave edge 205. The ultrasonic beam 100 then passes through the medium 400 and into the pipe 300. This progression is reversed as the ultrasonic beam 100 travels from the pipe 300 to the acoustic imaging device or imaging chip 600.

The focusing lens 200 used is unique to each pipe 300 or pipe inner surface 310. The focusing lens 200 is chosen to negate the scatter of the ultrasonic beam 100 by the curved pipe surfaces. The thickness of the pipe interior 315 or the wall of the pipe 300 (the distance from the inner surface 310 to the outer surface 305) may also have an effect upon the focusing lens 200 chosen.

Figure 3:
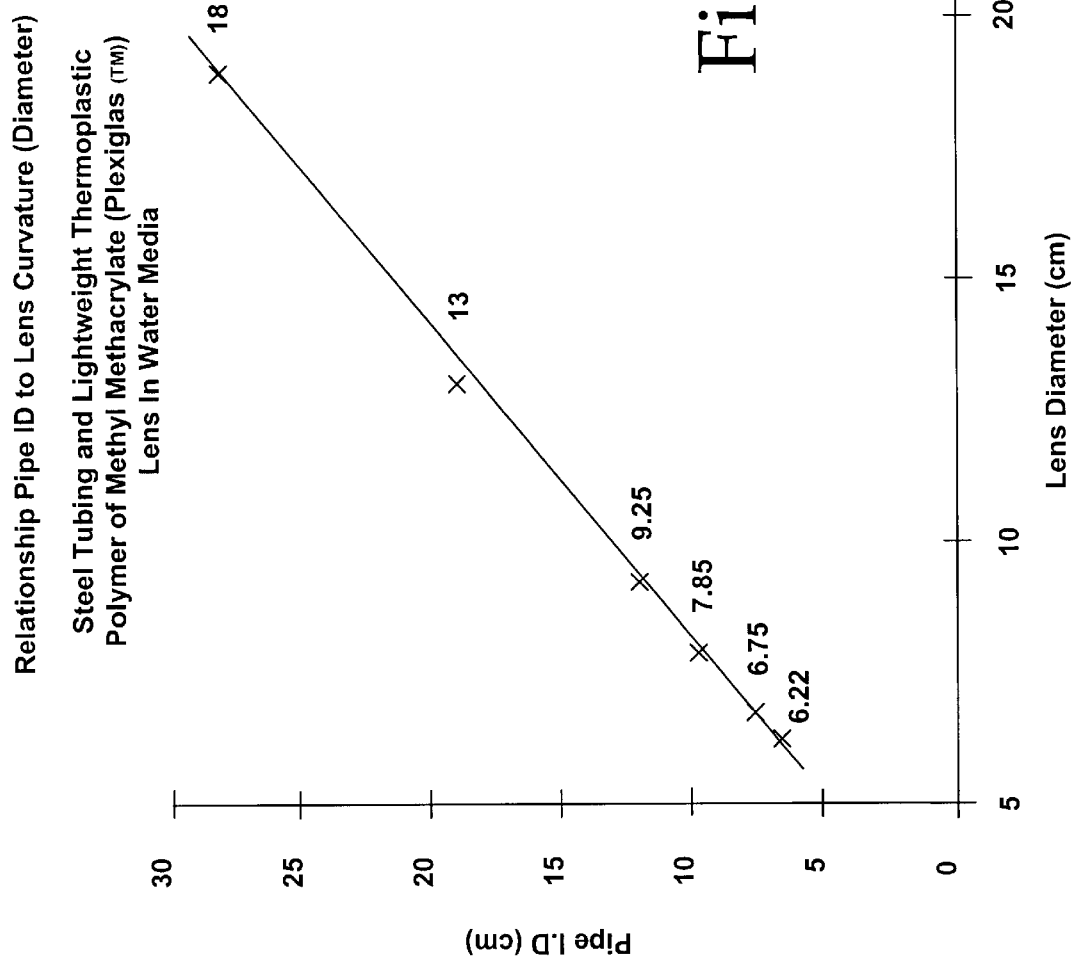
FIG. 3 is a graphical representation of the relationship of the pipe inner diameter to the lens curvature of the focusing lens; and, FIG. 4 is a graphical representation of the relationship of the pipe inner diameter to the lens distance from the pipe (different pipe thickness have different relationships).

The design of the focusing lens 200 is dependent on the relative velocity of sound in the medium 400, in the focusing lens 200, and in the test piece or pipe 300. The design is also dependent upon the diameter and wall thickness of the test piece or pipe 300. In the preferred embodiment, the preferred focusing lens curvature of the concave edge 205 is proportional to the pipe inner diameter. FIG. 3 shows a graphical representation of this relationship for a Plexiglas (™) focusing lens and steel tubing in a water media. The relationship can be shown by the following formula: Lens Diameter=0.551*PipeID+2.571 (dimensions in cm). Plexiglas (™) is a lightweight thermoplastic polymer of methyl methacrylate.

Figure 4:
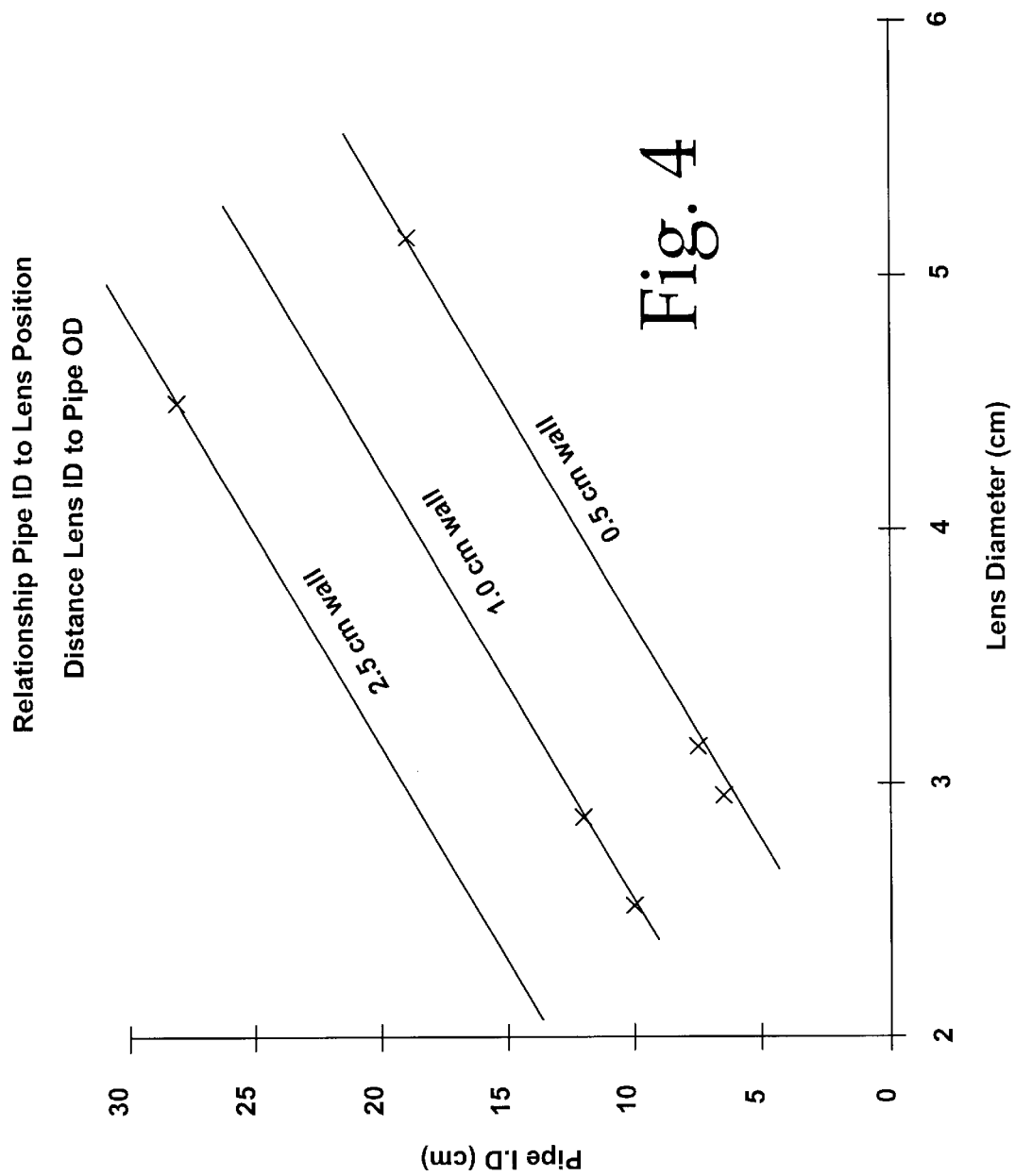

FIG. 4 is a graphical representation of the relationship of the pipe inner diameter to the distance of the focusing lens 200 from the middle point of the concave edge 205 to the outer diameter 305 of the pipe 300, It is important to note that different pipe wall thickness have different ratios as illustrated by FIG. 4. The relationship can be shown by the following formula: Lens Distance=0.174*PipeID+0.539*(PipeWallThickness) $^2$−2.8*PipeWallThickness+3.1 (dimensions in cm).

When introducing elements of the present invention or the preferred embodiment(s) thereof, the articles "a," "an," "the" and "said" are intended to mean there Are one or more of the elements. The terms "comprising," "including," and "having" are intended to be inclusive and mean that there may be additional elements other than the listed elements.

Although the present invention has been described in considerable detail with reference to certain preferred versions thereof, other versions are possible. Therefore, the spirit and scope of the appended claims should not be limited to the description of the preferred versions contained herein.

What is claimed is:

1. A method for acoustic imaging of a tubular shape, the tubular shape having an outer surface and an inner surface, the method comprising:

(a) generating an ultrasonic beam by a method comprising:

sending a timing signal from a Charge Couple Device acoustic imaging camera to a digital delay circuit which delays the timing signal for a programmed amount of time and then transmits the timing signal to an electronic pulser circuit;

generating an electronic pulse of programmed amplitude and shape by the electronic pulser circuit;

transmit the electronic pulse to a transducer; and, changing the electronic pulse via the transducer into an ultrasonic beam;

(b) directing the ultrasonic beam through a focusing lens, the focusing lens having a substantially planar edge and a substantially concave edge located on opposite sides of the focusing lens, the ultrasonic beam entering the focusing lens through the planar edge and exiting from the concave edge such that the ultrasonic beam enters the outer surface of the tubular shape, passes to the inner surface and the ultrasonic beam is reflected at the inner surface, passes back through the outer surface and passes back through the focusing lens in the opposite direction; and (b) converting the ultrasonic beam that has passed through the focusing lens in the opposite direction into a video output that displays an image of the inner surface, the outer surface and an internal volume image of the tubular shape.

2. The method claim of claim 1, wherein the programmed amount of delay time is an amount of time required for the electronic pulser circuit to generate an electrical pulse, send the pulse to the transducer, for the transducer to change the electrical signal into an ultrasonic beam, for the ultrasonic beam to travel to and through the focusing lens, to and through the tubular shape, back to and through the focusing lens, and to the Charge Couple Device acoustic imaging camera.

3. The method claim of claim 2, wherein the ultrasonic beam is coupled to the focusing lens and the tubular shape via a medium, the medium being a solid.

4. The method claim of claim 3, wherein the medium is manufactured from the same material as the tubular shape.

5. The method claim of claim 2, wherein the ultrasonic beam wherein the ultrasonic beam is coupled to the focusing lens and the tubular shape via a medium, the medium being a liquid.

6. The method claim of claim 5, wherein the focusing lens is Fabricated from a solid.

7. The method claim of claim 6, wherein the focusing lens is fabricated from any homogeneous material that does not cause random distortions of sound waves.

8. The method claim of claim 7, wherein the homogenous material is selected from the group consisting of plastic, glass, polymers and ceramic.

9. The method claim of claim 7, wherein the focusing lens is fabricated from a lightweight thermoplastic polymer of methyl methacrylate.

10. The method claim of claim 9, wherein the medium being water, the tubular shape having a inner diameter, the focusing lens having a concave edge including a curvature, the tubular shape being manufactured from steel, wherein the curvarure (diameter) of the concave edge has a direct relationship to the tubular shape inner diameter.

11. A method for acoustic imaging of a tubular shape, the tubular shape having an outer surface and an inner surface, the method comprising:

(a) generating an ultrasonic beam by a method comprising:
  sending a timing signal from a Charge Couple Device acoustic imaging camera to a digital delay circuit which delays the timing signal for a programmed amount of time and then transmits the timing signal to an electronic purser circuit;
  generating an electronic pulse of programmed amplitude and shape by the electronic pulser circuit;
  transmitting the electronic pulse to a transducer; and,
  changing the electronic pulse via the transducer into an ultrasonic beam;

(b) directing the ultrasonic beam through a focusing lens, the focusing lens being manufactured from a lightweight thermoplastic polymer of methyl methacrylate, the focusing lens having a substantially planar edge and a substantially concave edge located on opposite sides of the focusing lens, the ultrasonic beam entering the focusing lens through the planar edge and exiting from the concave edge such that the ultrasonic beam enters the outer surface of the tubular shape at an oblique angle to the outer surface, and the ultrasonic beam passes to the inner surface, is reflected at the inner surface, passes through the outer surface and passes through the focusing lens in the opposite direction, the ultrasonic beam being coupled to the focusing lens and the tubular shape via a medium, the medium being a liquid; and (c) converting the ultrasonic beam that has passed through the focusing lens in the opposite direction into a video output that displays an image of the inner surface, the outer surface and an internal volume image of the tubular shape.

12. The method claim of claim 11, wherein the medium being water, the tubular shape having a inner diameter, the focusing lens having a concave edge including a curvature, the tubular shape being manufactured from steel, wherein the curvature (diameter) of the concave edge has a direct relationship to the tubular shape inner diameter as shown by the following formula: Lens Diameter=0.551*PipeID+2.571.

13. The method claim of claim 12, wherein the ultrasonic beam is continuously passing through a medium when it is not in the focusing lens and the tubular shape.

14. The method of claim 13, wherein the inner diameter has a direct relationship to the distance from the focusing lens to the outer diameter.

15. A method for acoustic imaging of a tubular shape, the tubular shape having an outer surface and an inner surface, the method comprising:

(a) generating an ultrasonic beam by a method comprising:
  sending a timing signal from a Charge Couple Device acoustic imaging camera to a digital delay circuit which delays the timing signal for a programmed amount of time and then transmits the timing signal to an electronic pulser circuit;
  generating an electronic pulse of programmed amplitude and shape by the electronic pulser circuit;
  transmitting the electronic pulse to a transducer; and,
  changing the electronic pulse via the transducer into an ultrasonic beam;

(b) directing the ultrasonic beam through a focusing lens, the focusing lens being manufactured from a lightweight thermoplastic polymer of methyl methacrylate, the focusing lens having a substantially planar edge and a substantially concave edge located on opposite sides of the focusing lens, the ultrasonic beam entering the focusing lens through the planar edge and exiting from the concave edge such that the ultrasonic beam enters the outer surface of the tubular shape at a right angle to the outer surface and the ultrasonic beam passes to the inner surface, is reflected at the inner surface, passes through the outer surface and passes through the focusing lens in the opposite direction, the ultrasonic beam being coupled to the focusing lens and the tubular shape via a medium the medium being a liquid; and (c) converting the ultrasonic beam that has passed through the focusing lens in the opposite direction into a video output that displays an image of the inner surface, the outer surface and an internal volume image of the tubular shape.

16. The method claim of claim 15, wherein prior to entering the focusing lens the ultrasonic beam is reflected by a beam splitter placed at a about 45 degree angle relative to the ultrasonic beam.

17. The method claim of claim 16, wherein the ultrasonic beam is continuously passing through a medium when it is not in the focusing lens and the tubular shape.

18. The method claim of claim 17, wherein the medium being water, the tubular shape having a inner diameter, the focusing lens having a concave edge including a curvature, the tubular shape being manufactured from steel, wherein the curvature of the concave edge has a direct relationship to the tubular shape inner diameter as shown by the following formula: Lens Diameter=0.551*PipeID+2.571.

19. The method of claim 18, wherein the inner diameter has a direct relationship to the distance from the focusing lens to the outer diameter as shown by the following formula: Lens Distance=0.174*PipeID+0.539*(PipeWallThickness)$^2$−2.8*PipeWallThickness+3.1.

* * * * *